(12) United States Patent
Carlson et al.

(10) Patent No.: US 12,741,107 B2
(45) Date of Patent: Sep. 22, 2026

(54) MEDICAL SYSTEMS AND ASSEMBLIES FOR DELIVERING FLUID

(71) Applicant: Boston Scientific Scimed, Inc., Maple Grove, MN (US)

(72) Inventors: Steven T. Carlson, Minneapolis, MN (US); Jeremy Jevne, Ham Lake, MN (US); Blake Bolthouse, Grand Rapids, MI (US); Bruce Fullerton, Hudson, WI (US); WD Blackmon, III, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 19/298,679

(22) Filed: Aug. 13, 2025

(65) Prior Publication Data

US 2026/0048208 A1 Feb. 19, 2026

Related U.S. Application Data

(60) Provisional application No. 63/682,984, filed on Aug. 14, 2024.

(51) Int. Cl.
*A61M 13/00* (2006.01)

(52) U.S. Cl.
CPC ..... *A61M 13/003* (2013.01); *A61M 2205/332* (2013.01); *A61M 2205/3331* (2013.01); *A61M 2205/50* (2013.01)

(58) Field of Classification Search
CPC .... A61M 5/31; A61M 5/178; A61M 5/31511; A61M 5/31568; A61M 2205/50; A61M 2205/332; A61M 2205/3125; A61M 2205/3126; A61M 2205/3131; A61M 2205/3306; A61M 2205/3331; A61M 2205/3344; A61M 2205/3368; A61M 2205/3592; A61M 2205/581;
(Continued)

(56) References Cited

U.S. PATENT DOCUMENTS 5,814,015 A * 9/1998 Gargano ............ A61M 5/1456 604/67
D598,109 S 8/2009 Collins et al.
(Continued)

FOREIGN PATENT DOCUMENTS

EP 1066846 A1 1/2001
EP 4279003 A2 11/2023
JP 2009056176 A 3/2009

*Primary Examiner* — David P. Olynick
(74) *Attorney, Agent, or Firm* — Bookoff McAndrews, PLLC

(57) ABSTRACT

A medical assembly may include a syringe assembly, a rod, and a sensor. The syringe assembly may be removably positionable within a cavity of the medical assembly. The syringe assembly may include a barrel and a plunger. The plunger may be movably disposed within the barrel. The rod may have a first end and a second end. The second end of the rod may be configured to contact the plunger in some configurations of the medical assembly and separated from the plunger in other configurations of the medical assembly. A central longitudinal axis of the rod may extend through the sensor and the plunger in configurations in which the syringe is positioned in the cavity of the medical assembly.

20 Claims, 5 Drawing Sheets

(58) Field of Classification Search
CPC ...... A61M 2205/582; A61M 2205/583; A61M 2205/587
See application file for complete search history.

(56) References Cited

U.S. PATENT DOCUMENTS 7,618,409 B2* 11/2009 Hochman .............. A61C 19/08 604/67
D624,654 S 9/2010 Shimizu
D695,410 S 12/2013 Becker
D706,239 S 6/2014 Chen et al.
D711,003 S 8/2014 Chen et al.
D734,857 S 7/2015 Weichert et al.
D762,860 S 8/2016 He et al.
D835,281 S 12/2018 Clifford et al.
10,342,593 B2 7/2019 Hastings et al.
D908,892 S 1/2021 Duignan et al.
D918,396 S 5/2021 Gray et al.
D926,995 S 8/2021 He et al.
D989,326 S 6/2023 Lund et al.
D1,009,273 S 12/2023 Chun
D1,063,078 S 2/2025 Gray et al.
2002/0045861 A1* 4/2002 Tribe ................ A61M 5/14546 604/154
2002/0077852 A1* 6/2002 Ford ...................... G16H 40/63 705/2
2003/0205587 A1 11/2003 Tribe et al.
2003/0229311 A1* 12/2003 G. Morris ........... A61M 5/1456 604/151
2005/0177111 A1 8/2005 Ozeri et al.
2006/0211912 A1* 9/2006 Dlugos ............. A61M 39/0208 600/37
2007/0233147 A1* 10/2007 Vendrely ................. A61M 5/31 606/92
2008/0281265 A1* 11/2008 Hochman ............. A61M 5/158 604/110
2010/0214110 A1* 8/2010 Wang ................ A61M 5/16854 340/665
2010/0274180 A1* 10/2010 Donovan .......... A61M 5/16854 703/2
2011/0009821 A1* 1/2011 Jespersen ............ A61M 5/1452 604/131
2011/0264033 A1* 10/2011 Jensen .................. A61M 5/486 604/93.01
2012/0130204 A1 5/2012 Basta et al.
2013/0129532 A1* 5/2013 Flachbart .......... A61M 5/16854 417/279
2014/0249410 A1* 9/2014 Uber, III ................. A61M 5/20 604/246
2015/0133890 A1* 5/2015 Wander ............. A61M 5/16831 604/506
2015/0320934 A1* 11/2015 Draper ..................... G01D 5/32 604/154
2016/0220296 A1* 8/2016 Hastings ................ A61B 18/04
2016/0259913 A1* 9/2016 Yu ...................... A61M 5/31511
2018/0177944 A1* 6/2018 Sanborn ............ A61M 5/16859
2020/0093994 A1* 3/2020 Clarke ................ A61M 5/5013
2020/0238018 A1 7/2020 Lee et al.
2022/0122710 A1 4/2022 Desch et al.
2023/0398290 A1* 12/2023 Dugas ............... A61M 5/16813
2025/0128050 A1 4/2025 Mason et al.

* cited by examiner 100
102
104
106
108
110
112
114
116
118
120
120A
120B
122
122A
122B
122C
124
124
126
128
130A
130B
132A
132A
132A
132B
132B
134A
134B
136
138
138A
138B
138C
140

MEDICAL SYSTEMS AND ASSEMBLIES FOR DELIVERING FLUID

CROSS-REFERENCE TO RELATED APPLICATIONS

This patent application claims the benefit of priority to U.S. Provisional Application No. 63/682,984, filed on Aug. 14, 2024, which is incorporated by reference herein in its entirety.

TECHNICAL FIELD

The present disclosure relates generally to medical systems and assemblies for delivering fluid and, in particular, to systems and assemblies for measuring a pressure of a fluid within the system and/or assembly during fluid delivery.

BACKGROUND

Certain medical conditions, such as conditions of the prostate including benign prostatic hyperplasia (BPH), may be treated by ablation, including by vapor ablation. Such procedures may be performed using a system having a shaft that is inserted into a body lumen or otherwise into a body of a subject (e.g., patient). Certain systems may include a shaft that is inserted into, for example, a urethra of a subject and advanced through the urethra to the prostatic urethra (a portion of the urethra passing through the prostate). A fluid may be delivered into a portion of the system, and the fluid may be converted to vapor by an element of the system. The vapor is delivered to a tissue desired to be ablated (e.g., a prostate).

The systems and assemblies of the current disclosure may rectify some of the deficiencies described above, and/or address other aspects of the prior art.

SUMMARY

Each of the aspects disclosed herein may include one or more features described in connection with any of the other disclosed aspects.

The present disclosure includes medical assemblies. A medical assembly may comprise a syringe assembly, a rod, and a sensor. The syringe assembly may be removably positionable within a cavity of the medical assembly. The syringe assembly may include a barrel and a plunger. The plunger may be movably disposed within the barrel. The rod may have a first end and a second end. The second end of the rod may be configured to contact the plunger in some configurations of the medical assembly and to be separated from the plunger in other configurations of the medical assembly. A central longitudinal axis of the rod may extend through the sensor and the plunger in configurations in which the syringe assembly is positioned in the cavity of the medical assembly.

Any of the medical assemblies disclosed herein may include any or all of the following features. The sensor may be proximal of the rod. The sensor may be between the first end of the rod and a portion of an actuator configured to exert a distal force on the rod. The central longitudinal axis of the rod may extend through the portion of the actuator. The sensor may be configured to measure at least one of a force or a pressure. A least one of the force or the pressure measured by the sensor may be coaxial with or parallel to a force exerted by the rod on the plunger as the rod moves distally, thereby moving the plunger distally.

The sensor may be disposed between the second end of the rod and the plunger. An electric cable may be coupled to the sensor and extend along a length of the rod. The electrical cable may be secured to the rod via one or more cable retraining features.

The sensor may be disposed between a distal end of the barrel and a wall of the cavity.

The medical assembly may further comprise a controller configured to compare a value measured by the sensor to a threshold and, based on the comparison, cease actuation of the rod or reverse a direction of the rod.

The syringe assembly may be configured to fluidly couple to a medical device. Upon delivery of a fluid from the syringe assembly, the fluid may be delivered from a needle of the medical device.

The medical assembly may further comprise a bracket fixed to a sled. The rod may be movably fixed to the bracket. The rod may be secured to the bracket via a retaining feature. The retaining feature may be configured to permit longitudinal movement of the rod relative to the bracket. The rod may be cantilevered to the bracket.

The present disclosure also includes a medical assembly comprising a syringe assembly, a cavity, a rod, and a sensor. The syringe assembly may include a barrel and a plunger. The plunger may be movably disposed within the barrel. The cavity may be configured to removably receive the syringe assembly. The rod may have a first end and a second end. The second end of the rod may be configured to contact the plunger to expel a fluid from the barrel of the plunger. The sensor may be configured to measure a force or a pressure that is parallel or coaxial with a central longitudinal axis of the rod.

Any of the medical assemblies disclosed herein may include any or all of the following features. The sensor may be proximal of the rod, between the first end of the rod and a portion of an actuator configured to exert a distal force on the rod. The sensor may be between the second end of the rod and the plunger. The sensor may be between a distal end of the barrel and a surface of the cavity.

The present disclosure also includes a medical system comprising a medical device, a syringe assembly, and a control unit. The syringe assembly may include a barrel and a plunger movably disposed within the barrel. The control unit may include an actuator, a rod, and a sensor. The actuator may be configured to move the rod distally to move the plunger distally and expel a fluid from the barrel into the medical device. A central longitudinal axis of the rod may be parallel to or coaxial with a straight line extending though the plunger and sensor.

The medical system may include any or all of the previously described features.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to an operator and the term "distal" means a direction further from an operator. Although vapor ablation devices may be referenced herein, such references should not be construed as limiting. The terms approximately, substantially, about, and the like mean +/−10% from the stated value or other characteristic.

The examples disclosed herein may also be used along with other types of ablation mechanisms (e.g., cryoablation, RF ablation, or other types of ablation) or with other systems not relating to ablation. The examples disclosed herein may also be used to deliver, or expel, a fluid, for example, from a syringe.

BRIEF DESCRIPTION OF THE DRAWINGS

The accompanying drawings, which are incorporated in and constitute a part of this specification, illustrate examples of the present disclosure and, together with the description, serve to explain the principles of the disclosure.

DETAILED DESCRIPTION

A medical system for ablation of tissue may include a medical device and a control unit (e.g., a console). The control unit may include additional assemblies, or subassemblies, configured to control or measure one or more aspects of the medical system, including the medical device, the control unit, and/or the subject.

The medical device may be configured to deliver the vapor to a subject. The medical device may include a handle and a shaft extending distally from the handle. At least a portion of the shaft may be configured for insertion into the subject. A needle may be movably disposed within the shaft. The medical device may be fluidly coupled to the control unit. The control unit may be configured to expel a fluid from a syringe assembly disposed in the control unit and/or deliver the fluid from the syringe assembly to the medical device. For example, an assembly of the control unit may be configured to translate a rod at least partially within the syringe assembly to expel a fluid from the barrel of the plunger and/or deliver a fluid to the medical device. The assembly of the control unit may be configured to measure a pressure, or a force, acting upon one or more portions of the syringe assembly. In aspects, the measured force may be indicative of a pressure within the syringe assembly, the medical device, a fluidic pathway extending between the syringe assembly and medical device, and/or the subject.

In aspects, measuring a pressure acting upon portion(s) of the syringe assembly, the medical device, the fluidic pathway extending between the syringe assembly and medical device, and/or the subject may assist in preventing damage to one or more aspects of the system and/or the subject. For example, the pressure measuring aspects of the assembly may detect clogs or leaks. For example, should the pressure meet or exceed a first threshold and/or meet or fall below a second threshold, the assembly may be stopped and/or reversed.

Although the figures and the description below describe different aspects of exemplary systems and assemblies, the features of any of the systems and assemblies disclosed herein may be combined in any manner, unless stated otherwise.

Figure 1:
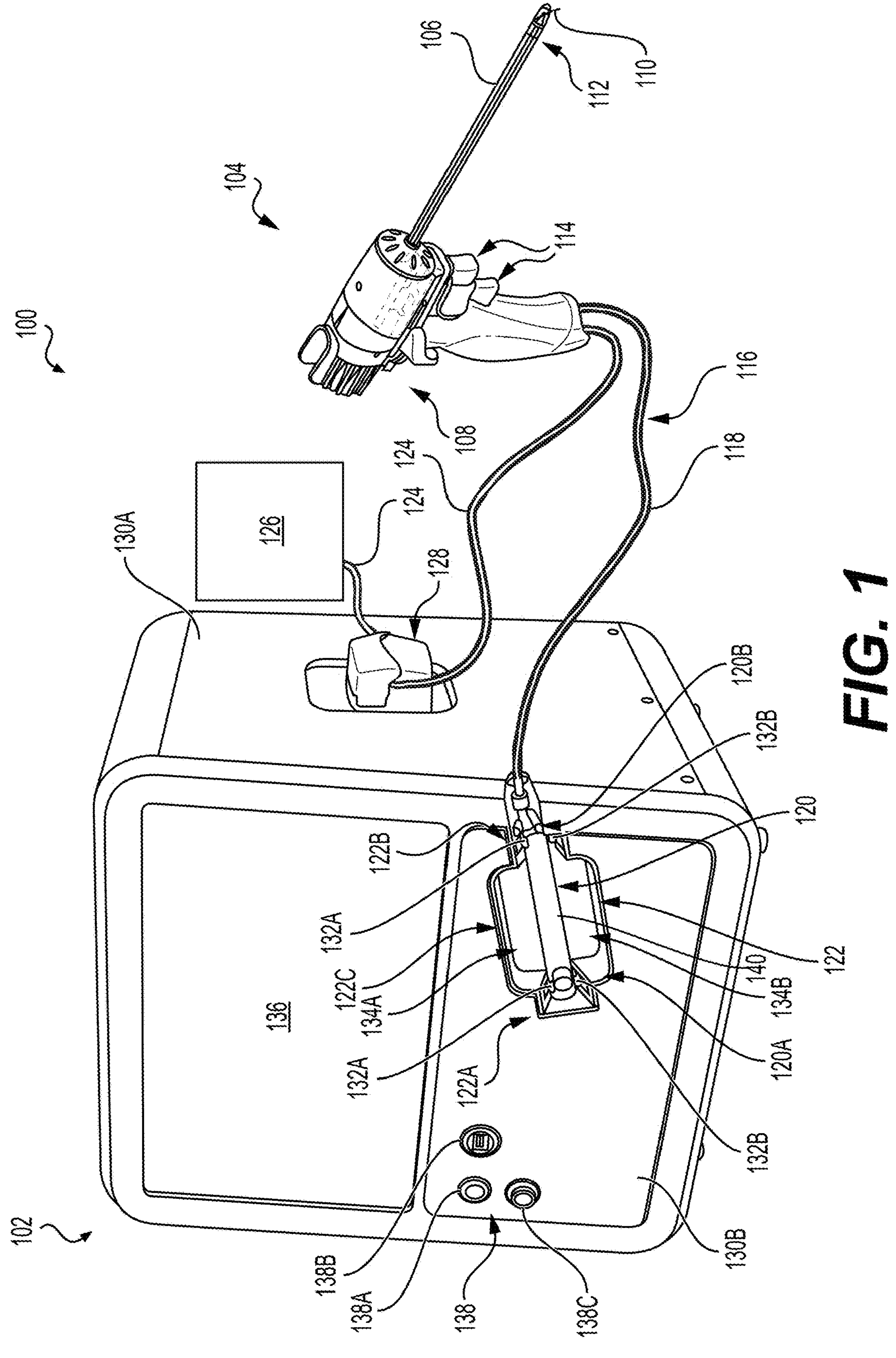
FIG. 1 depicts an exemplary medical system, according to aspects of this disclosure.

FIG. 1 illustrates an exemplary vapor delivery system, or medical system 100. Medical system 100 may include a control unit 102 (e.g., a console) and a vapor delivery device 104. Vapor delivery device 104 may have an elongate shaft 106 configured for insertion into a subject (e.g., into the urethra of a subject). A proximal end of elongate shaft 106 may be coupled (directly or indirectly) to a handle portion 108 for gripping by a user.

Medical device 104 may include a vapor delivery needle 110 moveably disposed within a lumen of elongate shaft 106. For example, vapor delivery needle 110 may be configured to extend from a distal portion 112 of elongate shaft 106. Vapor delivery needle 110 may extend in a perpendicular or transverse (non-zero angle) direction (e.g., away from a central longitudinal axis of elongate shaft 106). Vapor delivery needle 110 may include one or more vapor delivery ports, or openings, configured to deliver a flow of vapor media from vapor delivery needle 110 into tissue of the subject.

Vapor delivery device 104 may further include one or more triggers, buttons, levers, or actuation mechanisms 114 configured to actuate various functions of the system. For example, one of the one or more actuation mechanisms 114 may be configured to deliver the vapor medium from vapor delivery needle 110. Another of the one or more actuation mechanisms 114 may be configured to deliver one or more fluids (e.g., air, saline, a fluidic agent, coolant, etc.) from vapor delivery needle 110 or other outlets of elongate shaft 106. Further actuation mechanism(s) 114 may be configured to extend and/or retract vapor delivery needle 110, for example, from distal portion 112 of elongate shaft 106.

One or more fluidics tubes 116 may extend from handle portion 108. For example, a first fluidics tube 118 may extend from handle portion 108. First fluidics tube 118 may permit fluid communication between a syringe assembly 120 disposed within a cavity 122 of control unit 102. A second fluidics tube 124 may extend from handle portion 108, for example, to a fluid (e.g., gas or liquid) source 126. Fluid source 126 may be, for example, a pump, a saline bag or bottle, or other source containing a fluid. In some aspects, a portion of second fluidics tube 124 may be placed within a peristaltic pump 128 disposed on a first surface 130A (e.g., a side surface) of control unit 102. The illustrated position of peristaltic pump 128 is merely exemplary, as peristaltic pump 128 may be positioned elsewhere (e.g., on other surfaces) of control unit 102. Peristaltic pump 128 may be configured to provide a flow of cooling/irrigation fluid (e.g., saline, an agent, or other fluid) to vapor delivery device 104 (e.g., via second fluidics tube 124).

Cavity 122 of control unit 102 may be configured to removably receive syringe assembly 120. For example, syringe assembly 120 may be removably positionable within cavity 122. Cavity 122 may be disposed on a second surface 130B (e.g., a forward-facing surface) of control unit 102. The illustrated position of cavity 122 is merely exemplary, as cavity 122 may be positioned elsewhere (e.g., on other surfaces) of control unit 102. In some aspects, syringe assembly 120 may be disposed within cavity 122 at an angle. For example, a first end 120A of syringe assembly 120 may be below (e.g., at a lower height or elevation) as compared to a second, opposite end 120B of syringe assembly 120. In some aspects, first end 120A may define a proximal end of syringe assembly 120, and second end 120B may define a distal end of syringe assembly 120.

Cavity 122 of control unit 102 may include one or more securing features to assist with fixing, or containing, syringe assembly 120 within cavity 122. For example, a first securing feature 132A may be at a first, proximal end 122A of cavity 122, and a second securing feature 132B may be at a second, opposite or distal end 122B of cavity 122. First securing feature 132A may be configured to receive first end 120A of syringe assembly 120, and second securing feature 132B may be configured to receive second end 120B of syringe assembly 120. In aspects, securing features 132A, 132B may include one or more pairs of clamps, claws, hooks, arms, or any other feature configured to secure or contain syringe assembly 120 within cavity 122.

In some aspects, a central portion 122C of cavity 122 may have a greater diameter as compared to first end 122A and/or the second end 122B of cavity 122. In these aspects, a first space 134A and/or a second space 134B may be defined around or on opposing sides of syringe assembly 120 (e.g., when syringe assembly 120 is disposed within cavity 122). Spaces 134A, 134B may be configured to permit a user to grasp syringe assembly 120 (e.g., for loading and/or removal of syringe assembly 120 from cavity 122 of control unit 102).

As will be described in further detail below, when syringe assembly 120 is disposed within cavity 122, portions of control unit 102 may be activated so as to deliver or expel a fluid from syringe assembly 120. In these aspects, the fluid may be delivered from syringe assembly 120 to medical device 104 (e.g., via first fluidics tube 118).

Control unit 102 may further include a screen or display 136 disposed on second surface 130B, although display 136 may be disposed on other surfaces of control unit 102. Display 136 may be configured to display or otherwise provide operating parameters during a vapor therapy. In aspects, display 136 may be a display or a touch-screen.

Control unit 102 may further include one or more controls 138 (e.g., buttons, levers, switches, etc.) disposed on second surface 130B and/or other surfaces of control unit 102. Control(s) 138 may include one or more of a power button or switch 138A, an electronic port 138B, and/or a grounding port 138C. Control(s) 138 may include additional buttons or switches (e.g., a keyboard, a number pad, etc.), for example, to enable a user to input data or parameters into control unit 102 and/or to otherwise control aspects of medical system 100, including control unit 102.

Figure 2:
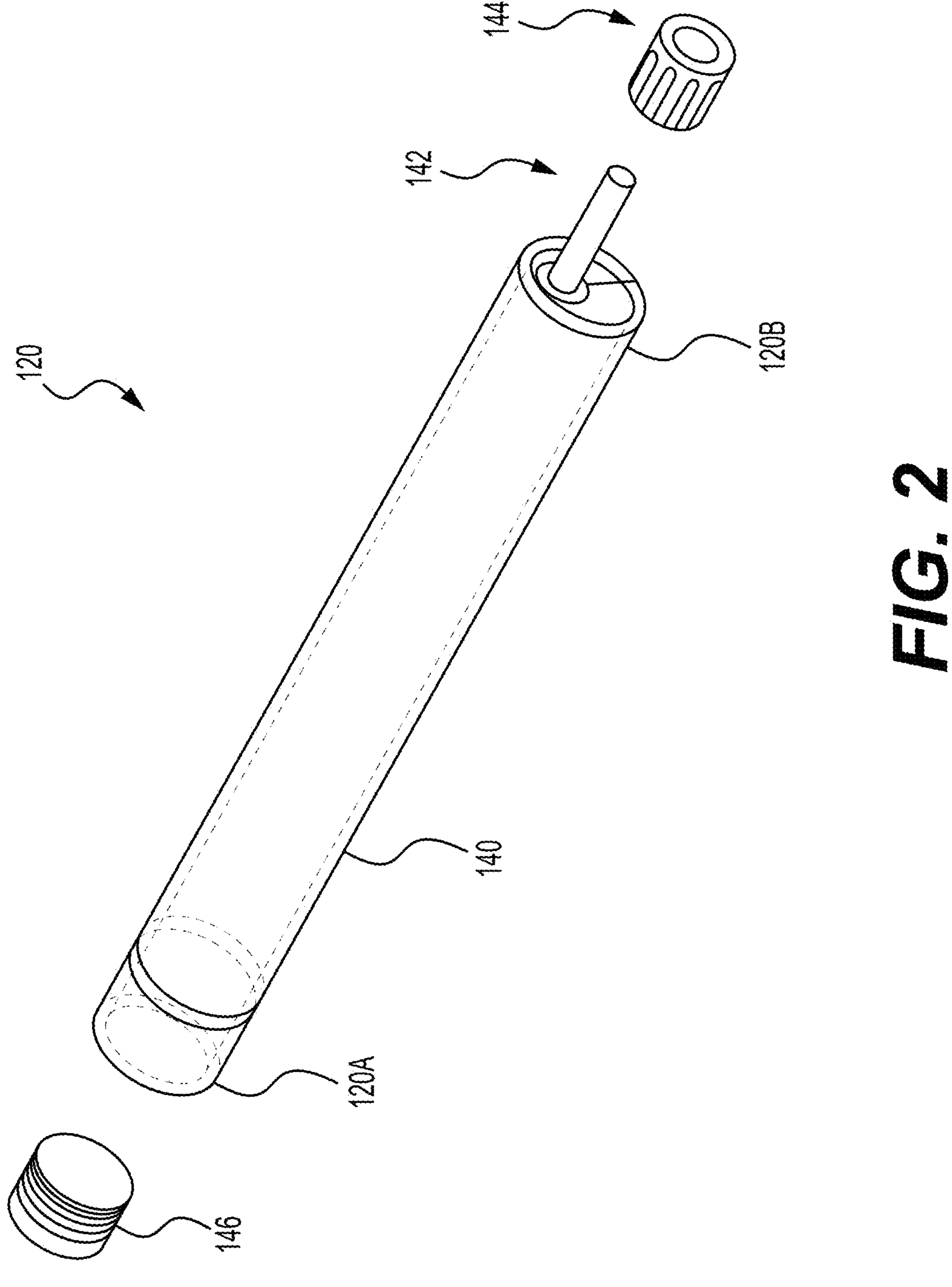
FIG. 2 depicts an exploded view of an exemplary syringe assembly used with the system of FIG. 1, according to aspects of this disclose.

FIG. 2 illustrates an exploded view of syringe assembly 120. Syringe assembly 120 may be configured for receipt within cavity 122 of control unit 102 (FIG. 1). In aspects, syringe assembly 120 may be configured to provide a precise amount of fluid (e.g., sterile water, an agent, or other liquid) to vapor delivery device 104 for conversion into vapor. Syringe assembly 120 may include a barrel 140 having an exit port 142. Exit port 142 may be offset from a centerline of barrel 140. Exit port 142 may have a smaller diameter as compared to barrel 140. A luer fitting 144 may be fixed to exit port 142. Luer fitting 144 may be configured to connect to first fluidics tube 118 (FIG. 1).

A plunger 146 may be disposed at least partially within barrel 140 (e.g., in an assembled configuration). Plunger 146 may be configured to move from a first (back) end of barrel 140 to a second (front), opposite end of barrel 140. The first end of barrel 140 may be on a side of barrel 140 that is farthest from exit port 142, and the second end of barrel 140 may be adjacent to exit port 142. Accordingly, plunger 146 may be configured to eject fluid from exit port 142 (e.g., when plunger 146 translates from the first end of barrel 140 to the second end of barrel 140). In other aspects, barrel 140 may be filled with a fluid, for example, when plunger 146 translates in an opposite direction, within barrel 140 (e.g., from the second end of barrel 140 to the first end of barrel 140).

Figures 3A, 3B:
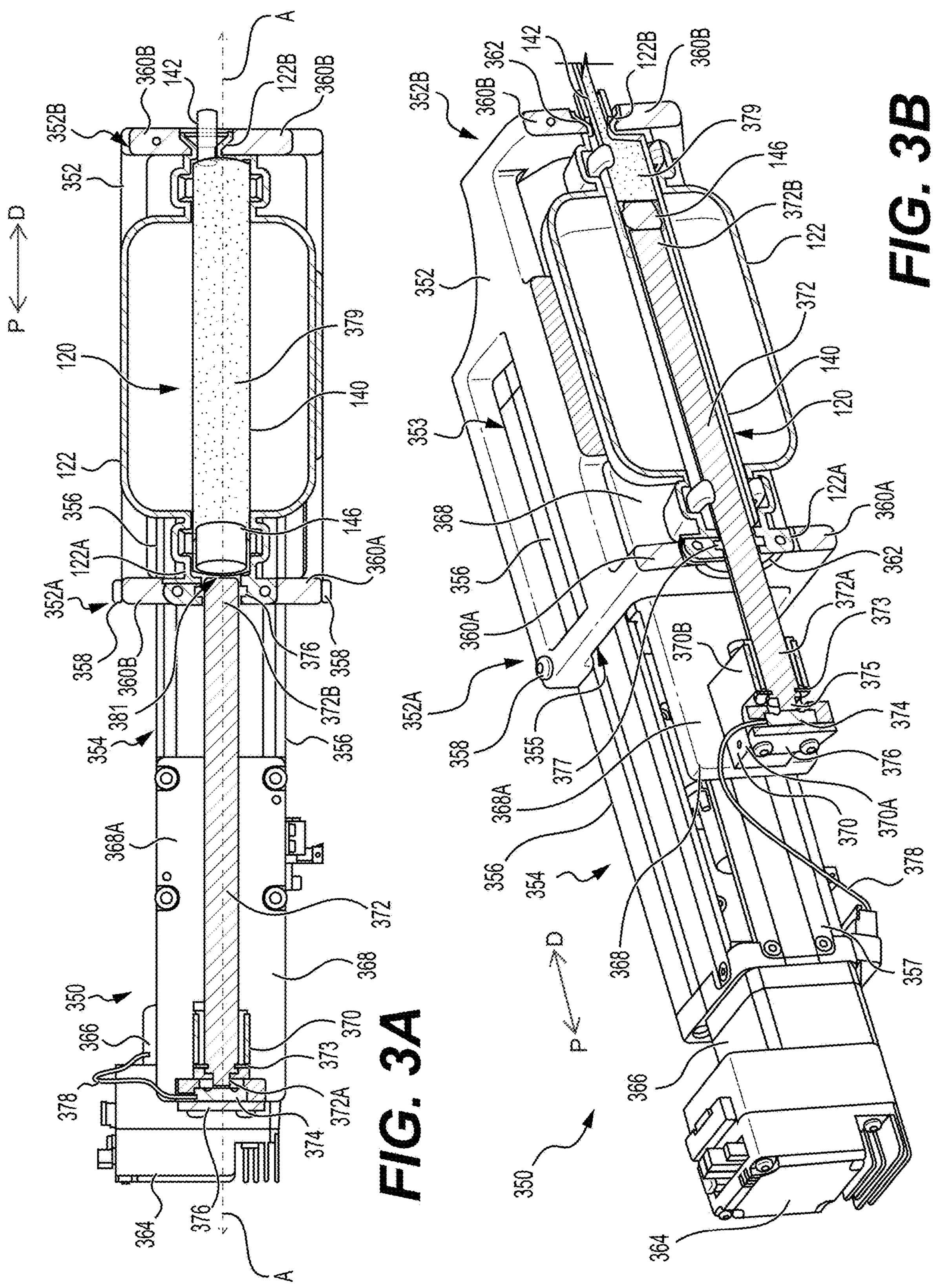
FIGS. 3A and 3B depict partial cross-sectional views of a fluid actuation assembly in a first configuration (FIG. 3A) and in a second configuration (FIG. 3B), according to aspects of this disclosure.

FIG. 3A depicts a front view of an actuation assembly 350 of control unit 102 (FIG. 1) in a first configuration, and FIG. 3B depicts a perspective view of actuation assembly 350 in a second configuration. In the first configuration (FIG. 3A) of actuation assembly 350, a first volume of a fluid 379 (e.g., a liquid, such as water) may be disposed within barrel 140 of syringe assembly 120. In the second configuration (FIG. 3B) of actuation assembly 350, a second volume of fluid 379 may be disposed within barrel 140 of syringe assembly 120. In transitioning from the first configuration to or toward the second configuration, fluid 379 may be delivered via exit port 142, into or through a connected fluidics tube (e.g., first fluidics tube 118 of FIG. 1), and into or through medical device 104 (FIG. 1). In these aspects, a vaporized form of fluid 379 may be delivered from needle 110 of distal portion 112. For example, medical device 104, control unit 102, or another element of system 100 may include a vapor generator to generate vapor from fluid 379. Aspects of FIGS. 3A and 3B may be referred to interchangeably throughout the following description of actuation assembly 350.

Actuation assembly 350 may be configured so as to enable the delivery of fluid 379 from needle 110 of distal portion 112. Described in further detail below, the configuration of actuation assembly 350 may be configured to measure parameters (e.g., a pressure or a force) regarding the delivery of fluid 379 and/or other aspects of system 100.

Referring to both FIGS. 3A and 3B, actuation assembly 350 may include a frame 352 at least partially encompassing a portion of a linear actuator 354. For example, a housing 356 and a rail 357 of linear actuator 354 may extend at least partially through a cutout 355 (FIG. 3B) of frame 352. Cutout 355 may extend longitudinally through at least a portion of frame 352 (e.g., from a first, proximal end 352A of frame 352 towards a second, distal end 352B of frame 352). In aspects, frame 352 may include a window 353 on a surface of frame 352 that is perpendicular to a surface defining a proximal end of cutout 355.

In aspects, frame 352 may be fixed to housing 356 (FIG. 3B) of linear actuator 354 via one or more mechanical fasteners 358 (e.g., screws or bolts). Two mechanical fasteners 358 are shown in FIG. 3A. However, additional or fewer mechanical fasteners may be utilized to fix frame 352 to housing 356. In aspects, frame 352 may be fixed to housing 356 via one or more other techniques or alternative fasteners, including, for example, an adhesive, a nail, a weld, etc.

Cavity 122 (described above with respect to FIG. 1) may be at least partially disposed between a first arm 360A and a second arm 360B of frame 352. In aspects, first arm 360A and second arm 360B may include one or more feature(s) 362 (e.g., cutouts, indents, protrusions, etc.) configured to receive a respective end of cavity 122. Feature(s) 362 may be sized and shaped to accept, or receive, appropriate ends of cavity 122. For example, feature(s) 362 of first arm 360A may be sized and shaped to accept, or receive, at least a portion of first end 122A of cavity 122, and features 362 of second arm 360B may be sized or shaped to accept, or receive, second end 122B of cavity 122. Cavity 122 is shown in cross-section in FIGS. 3A and 3B. Cavity 122 may protrude out of the page in FIG. 3A, so that cavity 122 is accessible via second surface 130B of control unit 102, and all other elements of actuation assembly 350 are received within (internal to) a housing of control unit 102.

Linear actuator 354 of actuation assembly 350 may further include a motor 364 and an encoder, or a controller, 366. Although not shown, one or both of motor 364 and encoder 366 may be electrically coupled to control unit 102. In some aspects, each of motor 364 and encoder 366 may be fixed to a first end (e.g., proximal end) of housing 356. Motor 364 may be configured to move a sled 368 from a first end (e.g., a proximal end) to a second (e.g., a distal end) of housing 356, for example, along rail 357. In these aspects, the proximal end may be opposite the direction of fluid flow, and the distal end may be in the direction of fluid flow. For example, sled 368 may be movably coupled to rail 357 of housing 356 and to a lead screw (not shown). The lead screw may extend at least partially through (or within) housing 356 and to, or at least partially through, motor 364.

In these aspects, motor 364 may be configured to rotate the lead screw clockwise or counterclockwise within housing 356. For example, as the lead screw rotates clockwise or counterclockwise, sled 368 may translate along rail 357 of housing 356 (e.g., from the first, proximal end to the second, distal end of housing 356, or vice versa). In particular, as the lead screw is rotated clockwise, sled 368 may translate in a first direction (e.g., towards or away from motor 364). Furthermore, as the lead screw is rotated counterclockwise, sled 368 may translate in a second, opposite direction (e.g., away from or towards motor 364). As will be described in further detail below, translation of sled 368 in at least one direction may result in fluid 379 being delivered from syringe assembly 120 (i.e., when syringe assembly 120 is disposed within cavity 122), and, thus, from medical device 104 (FIG. 1).

Referring still to FIGS. 3A and 3B, a support, or a bracket, 370 may extend from a surface 368A of sled 368. Surface 368A may be a front, or outward-facing surface. Support 370 may be fixed to sled 368 (e.g., via one or more mechanical fasteners, adhesives, welds, or other fixing techniques). In some aspects, support 370 may be integrally formed with sled 368. Support 370 may be L-shaped, or otherwise include a right angle. For example, support 370 may include a first arm 370A and a second arm 370B. First arm 370A may be fixed to surface 368A of sled 368, and second arm 370B may extend away from surface 368A of sled 368 at a right angle relative to surface 368A. In other words, second arm 370B may be cantilevered with respect to sled 368 and housing 356.

A rod 372 may extend through at least a portion of support 370 or otherwise be coupled to support 370 or another portion of sled 368. For example, a proximal portion of rod 372 may extend through second arm 370B of support 370. In aspects, second arm 370B of support 370 may include features (e.g., cutouts, indentations, protrusions, thru-holes etc.) for receiving rod 372. Rod 372 may be a solid metallic or plastic rod-like structure. In aspects, rod 372 may be cantilevered off, or relative to, support 370. A second, distal end 372B of rod 372 may extend away from support 370 in a distal direction. In some aspects, first end 372A of rod 372 may include a protrusion 375 extending proximally. Protrusion 375 may be narrower (e.g., have a smaller diameter) as compared to more distal portions of rod 372.

In some aspects, rod 372 may be longitudinally (axially) moveable relative to second arm 370B. For example, a retaining feature 373, (e.g., a retaining ring or similar component) may at least partially surround a diameter/width of rod 372. For example, retaining feature 373 may be configured to permit longitudinal movement of rod 372 within second arm 370B of support 370. Retaining feature 373 may further be configured to prevent rod 372 from moving in non-longitudinal directions or from being removed from support 370.

Rod 372 may be configured to extend into cavity 122 in at least some configurations of rod 372 (e.g., the configuration of FIG. 3B). For example, rod 372 may extend through second end 122B of cavity 122 in the configuration of FIG. 3B. In some aspects, second end 122B of cavity 122 may include an O-ring 377. O-ring 377 may be configured to prevent fluid flow proximally, for example, out of cavity 122 and into control unit 102. O-ring 377 may assist in preventing electrical damage of actuation assembly 350 and/or other aspects of control unit 102, for example, due to fluid ingress from syringe assembly 120.

Movement of sled 368 and, accordingly, support 370 proximally or distally may cause corresponding movement of rod 372. In aspects, rod 372 may extend distally from support 370 towards cavity 122 (and, thus, towards syringe assembly 120 removably disposed within cavity 122). Rod 372 may be a portion of control unit 102 and thus a separate element from syringe assembly 120, which may be removed from control unit 102 and separated from rod 372. Rod 372 may be reusable across procedures, while syringe assembly 120 (including barrel 140 and plunger 146) may be disposable. When syringe assembly 120 is removed from control unit 102, rod 372 may be spaced apart from plunger 146. In the first configuration (FIG. 3A), sled 368 may be in a first, or proximal, position. Accordingly, a space 381 may optionally be defined between second end 372B of rod 372 and plunger 146 of syringe assembly 120 (rod 372 may be spaced apart from plunger 146). In other aspects, second end 372B of rod 372 may abut plunger 146 in the first configuration.

To transition actuation assembly 350 from the first configuration (FIG. 3A) to or toward the second configuration (FIG. 3B), motor 364 may be activated such that sled 368 translates from the first, or proximal, end of housing 356 towards the second, or distal, end of housing 356. As sled 368 translates distally, rod 372 may simultaneously translate distally. Second end 372B of rod 372 may abut plunger 146 of syringe assembly 120. Accordingly, as rod 372 moves distally, rod 372 may push plunger 146 distally, such that plunger 146 may translate distally within barrel 140 of syringe assembly 120. As plunger 146 translates distally, fluid contained within barrel 140 (e.g., distally of plunger 146) may be forced out (ejected) via exit port 142.

A sensor 374 may be disposed between first end 372A of rod 372 and a portion of support 370, such as first arm 370A. As discussed in further detail below, sensor 374 may sense forces or pressures exerted by sensor 374 on first end 372A of rod 372. In some examples, sensor 374 may be a load cell. However, sensor 374 may include other types of force or pressure sensors. Sensor 374 may be a transducer that converts a force into a measurable electrical output. Sensor 374 may be electrically coupled to encoder 366, for example, via at least one electrical wire or cable 378. Encoder 366 may therefore receive electrical signals of sensor 374. In some aspects, encoder 366 may be configured to adjust one or more aspects (e.g., speed, direction, etc.) of motor 364. Accordingly, feedback from sensor 374 may result in a change of a speed or a direction of motor 364. Additionally or alternatively, cable 378 may be coupled to another element of control unit 102 (e.g., a processing unit)

that may provide control signals to aspects of control unit 102 or medical device 104 (e.g., to a vapor generator of medical device 104 or control unit 102).

A retaining plate 376 may be fixed to, or formed with, first arm 370A of support 370. Below, retaining plate 376 is described as being an element of first arm 370A; however, it will be appreciated that retaining plate 376 may be interpreted as a separate structure. Sensor 374 may be disposed between retaining plate 376 and first end 372A of rod 372. In some aspects, retaining plate 376 may be configured to exert a distal force on rod 372.

Sensor 374 is in-line with first arm 370A (e.g., retaining plate 376), rod 372, and syringe assembly 120. Rod 372 may exert a force on plunger 146 along a longitudinal axis (i.e., axially or longitudinally) of rod 372. A central longitudinal axis of rod 372 may intersect sensor 374 and a portion of linear actuator 354 (e.g., first arm 370A/retaining plate 376) that exerts a longitudinal or axial force on rod 372. A force or other parameter (e.g., pressure) measured by sensor 374 may be approximately parallel to the central longitudinal axis of rod 372 and approximately parallel to or coaxial with the force exerted by rod 372 on plunger 146. In other words, the force or pressure exerted on sensor 374 by rod 372 may be coaxial with or parallel to the force exerted by rod 372 on plunger 146. For example, the force or pressure exerted on sensor 374 by rod 372 may be coaxial with or parallel to the central longitudinal axis of rod 372. This arrangement may provide more reliable force measurements as compared to arrangements with sensors out-of-line with linear actuator 354 and/or syringe assembly 120 (e.g., sensors that measure lateral forces on barrel 140. "In-line" refers to the fact that a straight line "A" may be drawn that intersects each of sensor 374, first arm 370A/retaining plate 376, and plunger 146.

In the first configuration (FIG. 3A), first end 372A of rod 372 may be spaced from or gently abut sensor 374. In some examples, first end 372A of rod 372 may directly contact sensor 374. In other examples, one or more structures may be disposed between first end 372A and sensor 374. Sensor 374 may be configured to measure a magnitude of a load, force, or pressure acting upon rod 372 (or acting on sensor 374 by rod 372). Although the term "force" may be used herein, it will be appreciated that such a term also includes other values, such as pressure. For example, sensor 374 may be configured to measure a force acting upon rod 372 when sled 368 moves from the first, or proximal, end of housing 356 to the second, or distal end of housing 356. Sensor 374 may exert a force on first end 372A of rod 372 and first end 372A may exert a corresponding (e.g., equivalent) force on sensor 374.

The force measured by sensor 374 may relate to or reflect interactions of rod 372 with syringe assembly 120. Such a measurement may be indicative of a pressure within syringe assembly 120 (e.g., barrel 140), medical device 104, and/or a subject. As second end 372B of rod 372 abuts plunger 146, sensor 374 may abut first end 372A of rod 372. Accordingly, a force or pressure may be measured by sensor 374. The force or pressure measurement may be indicative of a force being applied to plunger 146 by rod 372. For example, when a pressure within barrel 140 is high (e.g., due to a clog in syringe assembly 120, first fluidics tube 118, or a portion of medical device 104), a greater force may be required to advance plunger 146. Accordingly, sensor 374 may measure a smaller value of force or pressure. When a pressure within barrel 140 is low (e.g., due to a leak in syringe assembly 120, first fluidics tube 118, or a portion of medical device 104), a smaller force may be required to advance plunger 146. Accordingly, sensor 374 may measure a smaller value of force of pressure.

Thus, the value measured by sensor 374 may be an indication of an amount of pressure within a fluidic path (e.g., within first fluidics tube 118 of FIG. 1, and/or within medical device 104) coupled to syringe assembly 120 and/or within a subject. For example, the force measurement may be indicative of a pressure within first fluidics tube 118, medical device 104 (e.g., within elongate shaft 106, delivery needle 110), and/or the subject. Based on the value measured by sensor 374, a speed or direction of sled 368 and rod 372 may be changed. The speed at which rod 372 travels may affect a speed at which fluid 379 is delivered from syringe assembly 120. Alternatively, other parameters may be adjusted by control unit 102. For example, control unit 102 may cease delivering power to a vapor generator in medical device 104 or control unit 102, to cease generation of and delivery of vapor.

In some aspects, for example, if the value measured by sensor 374 meets or exceeds a first threshold, movement of rod 372 may be changed. In some aspects, encoder 366 may be configured to compare a value measured by sensor 374 to a threshold and, based on the comparison, cease actuation of rod 372 or reverse a direction of rod 372. For example, a speed of the translation of rod 372 may be increased or decreased and/or translation of rod 372 may be stopped and/or reversed. For example, a value above the threshold may indicate a clog in system 100, and delivery of fluid may be halted by stopping movement of sled 368 or by cutting power to a vapor generator of medical device 104 or control unit 102. In these aspects, delivery of fluid 379 from syringe assembly 120 may be increased, slowed, and/or stopped and/or vapor generation may be ceased. Alternatively, if the value measured by sensor 374 meets or exceeds the first threshold, an alert may be displayed to a user.

In other examples, if the value measured by sensor 374 meets or is below a second threshold, movement of sled 368 may be altered, or generation of vapor may be halted. For example, a value below the threshold may be indicative of a leak in system 100. In such cases, movement of sled 368 (and rod 372) may be stopped, or generation of vapor by a vapor generator may be halted. Alternatively, if the value measured by sensor 374 meets or is below the second threshold, an alert may be displayed to a user.

Figure 4:
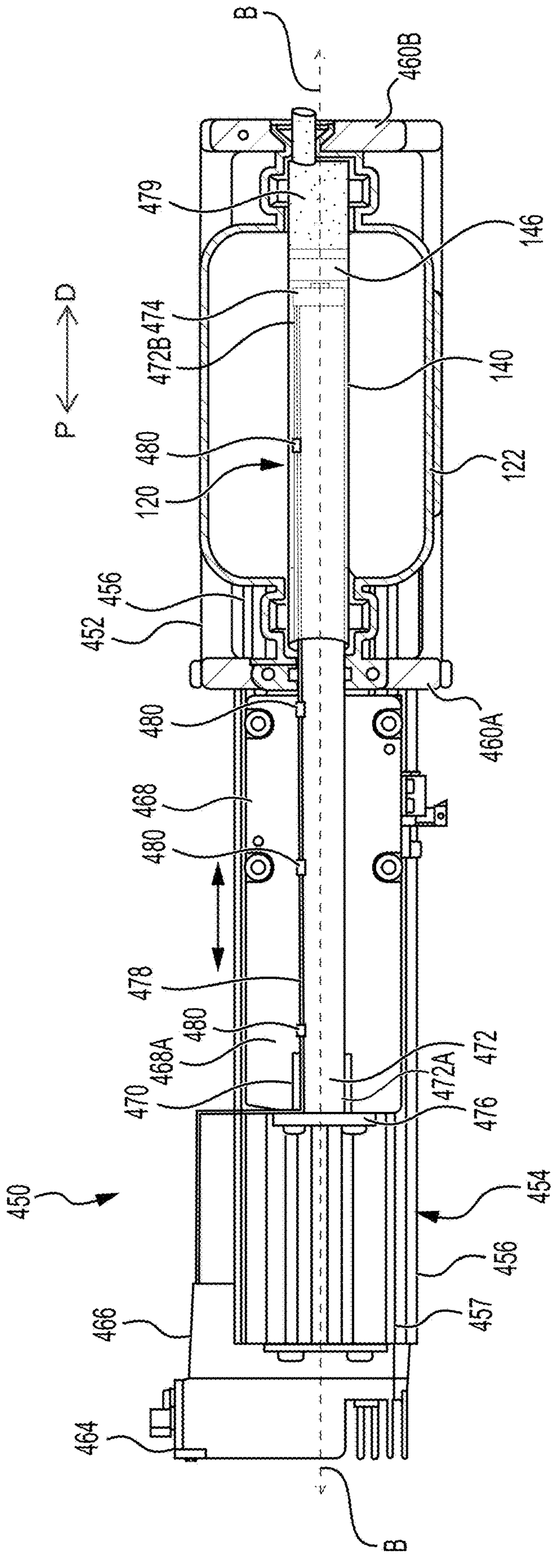
FIG. 4 depicts a partial cross-sectional view of an alternative fluid actuation assembly, according to aspects of this disclosure.

An alternative configuration of an actuation assembly 450 is illustrated in FIG. 4. FIG. 4 illustrates actuation assembly 450 in an actuated position (similar to the configuration of FIG. 3B). Actuation assembly 450 may have any or all of the same characteristics of actuation assembly 350, discussed above with respect to FIGS. 3A and 3B, except as described below. Accordingly, like numbers will be used to refer to like features, with "100" added to each numeral.

Actuation assembly 450 may include a frame 452 fixed to a rail 457 of a housing 456 of a linear actuator 454. Cavity 122 may be disposed between two arms (e.g., a first arm 460A and a second arm 460B) of frame 452. Syringe assembly 120 may be removably disposed within cavity 122.

A sled 468 may be moveably fixed to rail 457 of housing 456 of linear actuator 454. A support, or a bracket, 470 may be fixed to a surface 468A of sled 468. Support 470 may have any of the features of support 370. A rod 472 may be fixed to support 470 such that, for example, rod 472 is cantilevered relative to support 470. In some aspects, a retaining plate 476 may be configured to assist in maintaining a position of rod 472 relative to support 470. In aspects, a first end 472A of rod 472 may be fixed to retaining plate 476 (e.g., via mechanical fasteners, such as screws, pins, etc., or by adhesive).

Rod 472 may be configured to extend into barrel 140 of syringe assembly 120 in actuated configurations of actuation assembly 450. A sensor 474 may be fixed to second end 472B of rod 472. For example, sensor 474 may be coupled to second, distal end 472B of rod 472 using mechanical fasteners (e.g., screws, pins, brackets, etc.) or adhesive. When a syringe assembly 120 is loaded into cavity 122 (and rod 472 is advanced as necessary to engage plunger 146), sensor 474 may abut, or touch, plunger 146. For example, sensor 474 may directly contact rod 472 without intervening structures.

Accordingly, when rod 472 moves distally, thereby exerting a distal force on plunger 146 to deliver a fluid 479 from syringe assembly 120, sensor 474 may measure a magnitude of a load, force, or pressure exerted by plunger 146 on sensor 474 (or on plunger 146 by sensor 474). As discussed above, the magnitude of the force, load, or pressure may be indicative of a pressure of fluid 479 within syringe assembly 120 or other aspects of system 100 (FIG. 1). Any of the above actions may be taken as a result of the values measured by sensor 474. As with actuation assembly 350, described above, higher values measured by sensor 474 may be associated with higher pressures in fluidics system 100, and lower values measured by sensor 474 may be associated with lower pressures in fluidics of medical system 100.

Sensor 474 may be in-line with rod 472, and syringe assembly 120 (e.g., plunger 146). For example, an axis or straight line "B" may be drawn through rod 472, sensor 474, and plunger 146 (e.g., along a central longitudinal axis of rod 472). A force or pressure exerted on sensor 474 by rod 472 may be coaxial with or parallel to the force exerted by rod 472 on plunger 146. For example, the force or pressure exerted on sensor 574 by rod 472 may be coaxial with or parallel to a central longitudinal axis of rod 472. Sensor 474 may be coupled to an encoder 466 via one or more electrical wires or cables 478. Cable(s) 478 may extend through rod 472 (e.g., via a groove or lumen). Alternatively, cable(s) 478 may extend alongside a longitudinal length of rod 472. In some aspects, cable(s) 478 may include one or more retaining features 480 arranged along the longitudinal length of rod 472. Retaining features 480 may include a glue bead, a clip, a tab, or any other feature configured to maintain a position of cable(s) 478 relative to rod 472.

Figure 5:
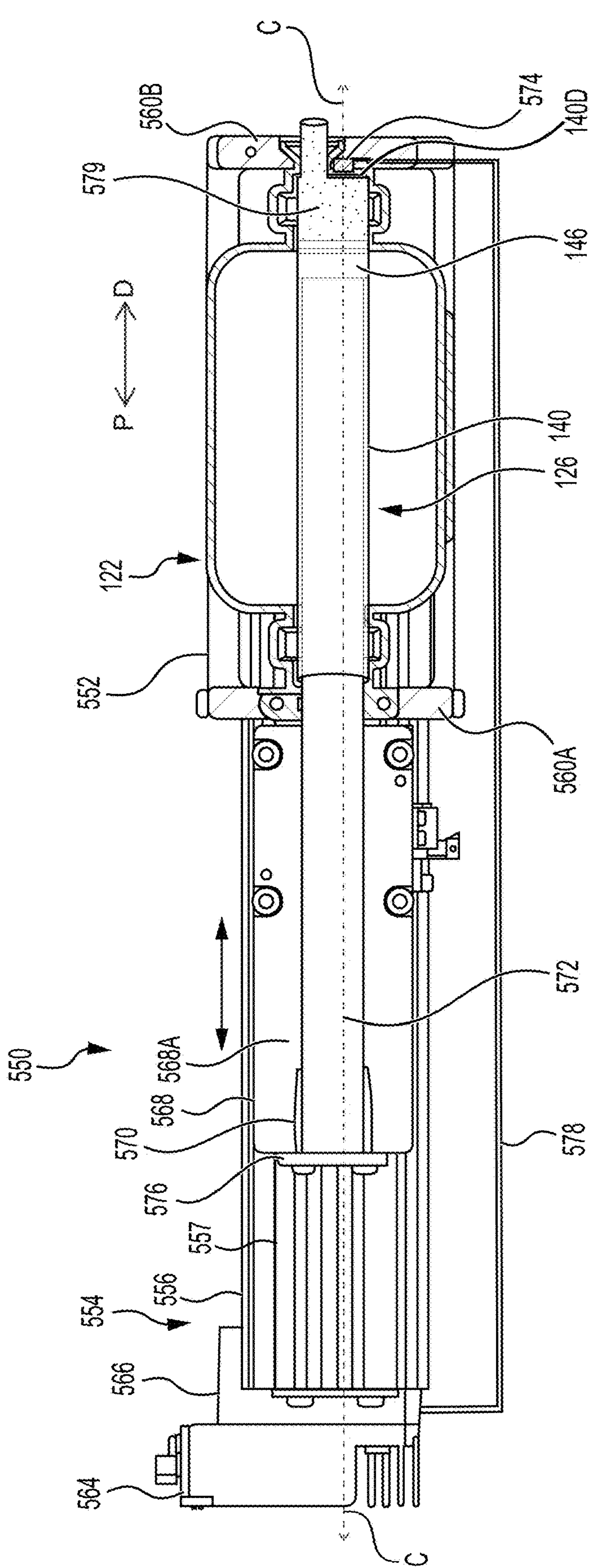
FIG. 5 depicts a partial cross-sectional view of another alternative exemplary fluid actuation assembly, according to aspects of this disclosure.

A further alternative configuration of an actuation assembly 550 is illustrated in FIG. 5. In particular, FIG. 5 illustrates actuation assembly 550 in a second, or actuated, position. Actuation assembly 550 may have any or all of the same characteristics of actuation assembly 350 and/or actuation assembly 450, discussed above, except as described below. Accordingly, like numbers will be used to refer to like features, with "100" added to each numeral relative to actuation assembly 450, and "200" added to each numeral relative to actuation assembly 350.

Actuation assembly 550 may include a frame 552 fixed to a housing 556 of a linear actuator 554. Cavity 122 may be disposed between two arms (e.g., a first arm 560A and a second arm 560B) of frame 552. Syringe assembly 120 may be removably disposed within cavity 122.

A sled 568 may be moveably fixed to housing 556 of linear actuator 554. A support, or bracket, 570 may be fixed to a surface 568A of sled 568. A rod 572 may be fixed to support 570 such that, for example, rod 572 is cantilevered relative to support 570. In some aspects, a retaining plate 576 may be configured to assist in maintaining a position of rod 572 relative to support 570. In aspects, a first end of rod 572 may be fixed to retaining plate 576, as described above for rod 472. Rod 572 may be configured to extend into barrel 140 of syringe assembly 120 in at least partially actuated configurations of actuation assembly 550.

A sensor 574 may be disposed between first arm 560A (or a surface of cavity 122 or control unit 102) and a distal face 140D of barrel 140, for example, within cavity 122. In some aspects, at least in actuated configurations of actuation assembly 550, sensor 574 may abut, or touch, distal face 140D of barrel 140 when syringe assembly 120 is disposed in cavity 122. In some examples, sensor 574 may be positioned such that an axis or straight line "C" may extend through sensor 574, barrel 140, and rod 572 (e.g., along a central longitudinal axis of rod 572). In other examples, sensor 574 may be offset such that a central longitudinal axis of rod 572 does not intersect sensor 574. In some examples, a line that is parallel to the central longitudinal axis of rod 572 and extends through sensor 574 may not intersect or pass through rod 572.

Sensor 574 may be coupled to an encoder 566 via one or more electrical wires or cables 578. Sensor 574 may be electrically coupled to encoder 566, for example, cable(s) 578. Encoder 566 may therefore receive electrical signals of sensor 574. In some aspects, encoder 566 may be configured to adjust one or more aspects (e.g., speed, direction, etc.) of a motor 564. Motor 564 may be configured to rotate a lead screw within housing 556 such that sled 568 translates along rail 557 of housing 556.

When rod 572 moves distally toward or into the second configuration (as pictured), thereby pressing against plunger 146 of syringe assembly 120, sensor 574 may measure a load or a force acting upon syringe assembly 120. In particular, when rod 572 transitions to the second configuration, syringe assembly 120 may be forced or pressed distally within cavity 122, for example, against sensor 574. An amount of force being exerted by rod 572 on plunger 146 may correspond to a force or pressure exerted by barrel 140 against sensor 574. Accordingly, the force or load may be indicative of a pressure of fluid 579 within syringe assembly 120 or other aspects of system 100 (FIG. 1). The force or pressure exerted by barrel 140 on sensor 574 may be approximately parallel to or coaxial with a central force exerted by rod 572 on plunger 146. For example, the direction of the force or pressure exerted by barrel 140 on sensor 574 may be coaxial with or parallel to the central longitudinal axis of rod 572.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical assembly, comprising:

a syringe assembly removably positionable within a cavity of the medical assembly, the syringe assembly including a barrel and a plunger, wherein the plunger is movably disposed within the barrel;

a rod having a first end and a second end, wherein the second end of the rod is configured to contact the plunger in some configurations of the medical assembly and to be separated from the plunger in other configurations of the medical assembly;

a sensor, wherein a central longitudinal axis of the rod extends through the sensor and the plunger in configurations in which the syringe assembly is positioned in the cavity of the medical assembly; and a bracket fixed to a sled, wherein longitudinal movement of the sled causes longitudinal movement of the rod, wherein the longitudinal movement of the rod moves the plunger, wherein the rod is coupled to the bracket via a retaining feature, and wherein the retaining feature is configured to permit longitudinal movement of the rod relative to the bracket as the longitudinal movement of the sled causes the longitudinal movement of the rod.

2. The medical assembly of claim 1, wherein the sensor is proximal of the rod.

3. The medical assembly of claim 2, wherein the sensor is between the first end of the rod and a portion of the bracket.

4. The medical assembly of claim 1, wherein the sensor is configured to measure at least one of a force or a pressure.

5. The medical assembly of claim 4, wherein at least one of the force or the pressure measured by the sensor is coaxial with or parallel to a force exerted by the rod on the plunger as the rod moves distally, thereby moving the plunger distally.

6. The medical assembly of claim 1, wherein the sensor is disposed between the second end of the rod and the plunger.

7. The medical assembly of claim 6, wherein an electrical cable coupled to the sensor extends along a length of the rod.

8. The medical assembly of claim 7, wherein the electrical cable is secured to the rod via one or more cable retaining features.

9. The medical assembly of claim 1, wherein the sensor is disposed between a distal end of the barrel and a wall of the cavity.

10. The medical assembly of claim 1, further comprising a controller configured to compare a value measured by the sensor to a threshold and, based on the comparison, cease actuation of the rod or reverse a direction of the rod.

11. The medical assembly of claim 1, wherein the syringe assembly is configured to fluidly couple to a medical device, and wherein, upon delivery of a fluid from the syringe assembly, the fluid is delivered from a needle of the medical device.

12. The medical assembly of claim 1, wherein the retaining feature is configured to permit longitudinal movement of the rod relative to the bracket.

13. The medical assembly of claim 1, wherein the rod is cantilevered relative to the bracket.

14. A medical assembly, comprising:

a syringe assembly including a barrel and a plunger, wherein the plunger is movably disposed within the barrel;

a cavity configured to removably receive the syringe assembly;

a rod having a first end and a second end, wherein the second end of the rod is configured to contact the plunger to expel a fluid from the barrel of the plunger;

a sensor, wherein the sensor is configured to measure a force or a pressure that is parallel to or coaxial with a central longitudinal axis of the rod; and a bracket, wherein the rod is irremovably coupled to the bracket, wherein the bracket is configured such that the rod is longitudinally movable with respect to the bracket, and wherein a force from a proximal wall of the bracket on the rod causes longitudinal movement of the rod to advance the plunger to expel the fluid from the barrel of the plunger.

15. The medical assembly of claim 14, wherein the sensor is proximal of the rod, between the first end of the rod and a portion of an actuator configured to exert a distal force on the rod.

16. The medical assembly of claim 14, wherein the sensor is between the second end of the rod and the plunger.

17. The medical assembly of claim 14, wherein the sensor is between a distal end of the barrel and a surface of the cavity.

18. The medical assembly of claim 14, wherein the second end of the rod is configured to contact the plunger in some configurations of the medical assembly and to be separated from the plunger in other configurations of the medical assembly.

19. A medical system, comprising:

a medical device;

a syringe assembly including a barrel and a plunger movably disposed within the barrel; and a control unit, wherein the control unit includes:

a rod;

a sensor, wherein a central longitudinal axis of the rod is parallel to or coaxial with a straight line extending through the plunger and the sensor; and a bracket, wherein the rod is coupled to the bracket such that (a) the rod is longitudinally movable relative to the bracket, and (b) non-longitudinal movement of the rod relative to the bracket is inhibited; and an actuator configured to move the bracket, thereby moving the plunger distally to expel a fluid from the barrel into the medical device while the rod is longitudinally movable relative to the bracket.

20. The medical system of claim 19, wherein the rod is irremovably coupled to the bracket.

* * * * *